United States Patent
Kothari et al.

(10) Patent No.: US 10,021,965 B2
(45) Date of Patent: Jul. 17, 2018

(54) HOLD A DENTAL CLEANING DEVICE ON FOOD RELATED ACCESSORIES

(71) Applicants: Nevaan Kothari, Henrico, VA (US); Riaan Kothari, Henrico, VA (US)

(72) Inventors: Nevaan Kothari, Henrico, VA (US); Riaan Kothari, Henrico, VA (US)

(*) Notice: Subject to any disclaimer, the term of this patent is extended or adjusted under 35 U.S.C. 154(b) by 0 days.

(21) Appl. No.: 15/829,796

(22) Filed: Dec. 1, 2017

(65) Prior Publication Data

US 2018/0084900 A1    Mar. 29, 2018

Related U.S. Application Data

(63) Continuation-in-part of application No. 14/851,350, filed on Sep. 11, 2015.

(51) Int. Cl.
*A45D 44/18* (2006.01)
*A46B 15/00* (2006.01)
*A61C 15/04* (2006.01)
*A61C 19/02* (2006.01)

(52) U.S. Cl.
CPC .......... *A46B 15/0055* (2013.01); *A45D 44/18* (2013.01); *A61C 15/048* (2013.01); *A61C 19/02* (2013.01)

(58) Field of Classification Search
CPC .. A45D 44/18; A46B 15/0055; A61C 15/048; A23G 1/505; A23G 3/56; A23G 3/563; A23G 4/186; A23G 2220/12
See application file for complete search history.

(56) References Cited

U.S. PATENT DOCUMENTS

| | | | | | |
|---|---|---|---|---|---|
| 4,346,493 | A | * | 8/1982 | Goudsmit | A46B 1/00 15/104.93 |
| 6,129,241 | A | * | 10/2000 | Rai | A46B 15/0055 221/185 |
| 8,308,651 | B1 | * | 11/2012 | Baruti | A46B 7/04 600/529 |
| 2003/0183242 | A1 | * | 10/2003 | Kemp | A46B 5/00 132/311 |
| 2012/0103356 | A1 | * | 5/2012 | Crisp | A46B 15/0055 132/200 |
| 2015/0196150 | A1 | * | 7/2015 | Chang | A47G 21/06 30/122 |

OTHER PUBLICATIONS

Colgate used toothbrush-shaped popsicle stickes to remind comsumers to Brush. Erin Zimmer 2009.*

* cited by examiner

*Primary Examiner* — Rachel Steitz
(74) *Attorney, Agent, or Firm* — James M. Smedley LLC; James Michael Smedley, Esq.

(57) ABSTRACT

A lollipop toothbrush apparatus includes an edible lollipop head, a hollow handle extending from the lollipop head, and a toothbrush having a handle that fits inside the hollow lollipop handle. The hollow lollipop handle has internal threading configured to receive a complementary threaded portion of the toothbrush handle. The toothbrush is configured to screw into the hollow lollipop handle and form a combined continuous handle for the lollipop.

9 Claims, 8 Drawing Sheets

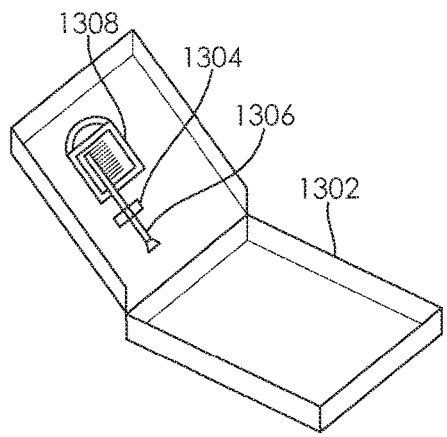
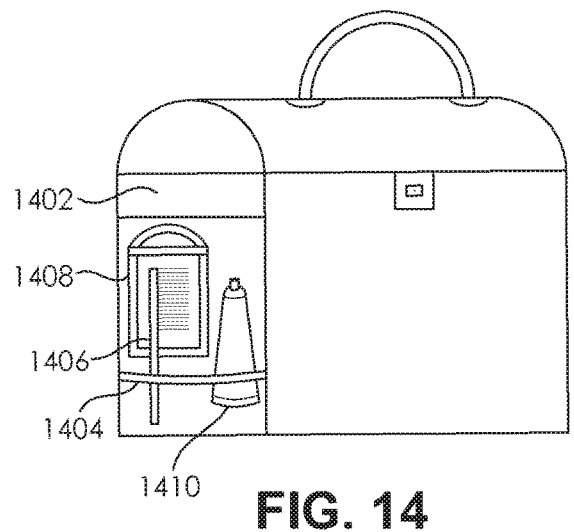
FIG. 13  FIG. 14
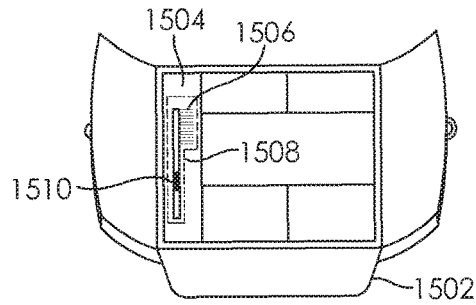
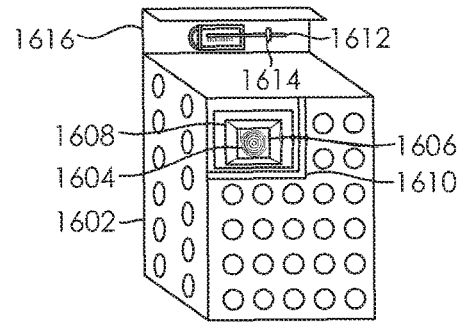
FIG. 15  FIG. 16
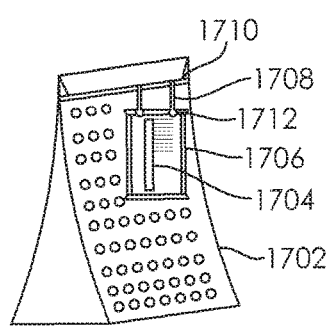
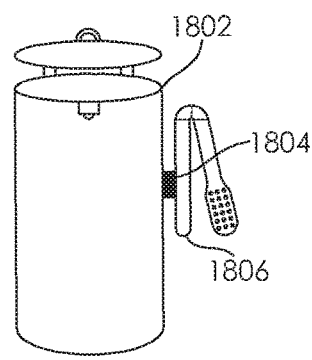
FIG. 17  FIG. 18

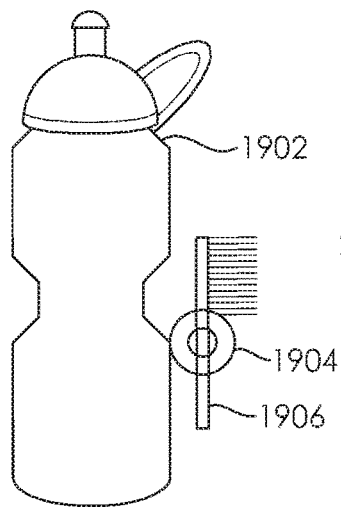
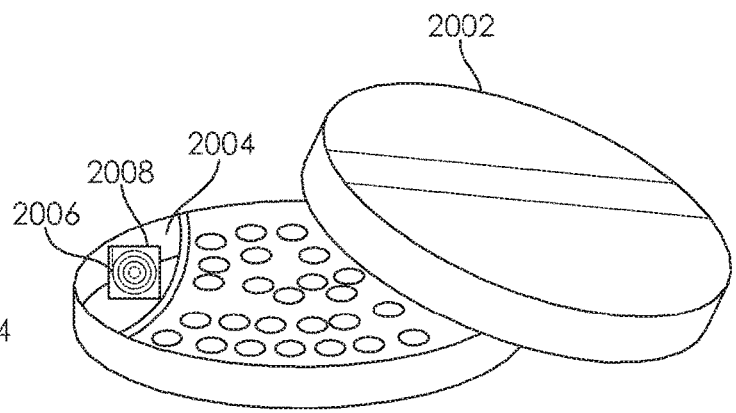
FIG. 19  FIG. 20
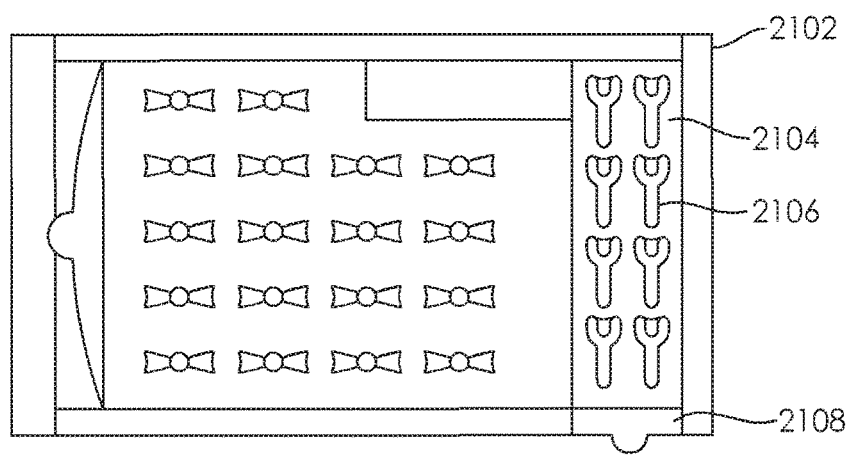
FIG. 21

HOLD A DENTAL CLEANING DEVICE ON FOOD RELATED ACCESSORIES

CROSS-REFERENCE TO RELATED APPLICATION

The present application is a Continuation-in-Part (CIP) of U.S. application Ser. No. 14/851,350 entitled HOLD A DENTAL CLEANING DEVICE ON FOOD/DRINK RELATED ITEMS OR ACCESSORIES filed on Sep. 11, 2015.

FIELD OF THE INVENTION

The present application relates to holding a dental cleaning device on food accessories, such as food utensils, food containers, and bags used for carrying foods.

BACKGROUND

Dental cavities, gum problems and tooth decay problems have been increasing at an alarming rate. One of the biggest problems facing children and adults is that they eat foods throughout the day, but they only clean their teeth or gums once or twice a day. However, plaque bacteria build up on the teeth or gums the entire day, especially when sugary or starchy foods are stuck in the teeth and.

One problem is that dental cleaning devices aren't readily available, and since a dental cleaning device isn't currently held (for example: attached, affixed, inserted, placed, embedded, etc.) on food accessories such as food utensils, food containers, and bags used for carrying foods, there isn't any option or visual reminder for users to clean their teeth and/or gums. In fact, dental cleaning devices are usually only found in washrooms or bathrooms. In short, due to the unavailability of dental cleaning devices next to or on food accessories, teeth or gum cleaning isn't done on a frequent basis, which not only leads to a lot of dental problems but also huge dental expenses.

BRIEF SUMMARY

This solution demonstrates a mechanism and exemplary apparatus to hold (for example: attach, affix, insert, place, embed, etc.) a dental cleaning device on food accessories such as food utensils, food containers, and bags used for carrying food or drinks. With this solution, it will not only make the dental cleaning devices easily accessible to users, but also provide a visual reminder to clean teeth or gums. In short, whether its children or adults, this solution of making dental cleaning devices available right next to or on food accessories will promote and inculcate good habits of frequently cleaning teeth or gums, and therefore, help to maintain good oral hygiene in the long run.

This solution will mainly include a dental cleaning device and a food accessory. Additionally, in situations where a dental cleaning device is attached to the food accessory, this solution can also include a built-in or add-on attachment to attach the dental cleaning device to the food accessory. Additionally, in situations where a dental cleaning device is inserted or placed on the food accessory, this solution can also include a placeholder indicator on the food accessory to indicate that the specially designated section has been allocated for keeping the dental cleaning devices. Moreover, when a dental cleaning device is inserted within the food accessory, this solution can also include an inserting mechanism, which helps to hold the dental cleaning device within that food accessory. In addition, to protect the bristles or protect the entire dental cleaning device, this solution can also include a cover for either a part of or the entire dental cleaning device.

According to an embodiment of the present invention, a mechanism is provided to hold the food accessory and the dental cleaning device together that includes a food accessory, a dental cleaning device, and a holding mechanism that holds the food accessory and the dental cleaning device together.

According to an embodiment of the present invention, the holding mechanism includes partially or completely attaching the dental cleaning device and the food accessory together using an attachment.

According to an embodiment of the present invention, an attachment can be attached either to the food accessory or to the dental cleaning device or to both of them.

According to an embodiment of the present invention, one of the examples of an attachment includes an attracting magnet attached to either the food accessory or to the dental cleaning device or to both of them.

According to an embodiment of the present invention, an attachment is capable of holding a dental cleaning device either directly on it or using further embedded or attached components on it.

According to an embodiment of the present invention, the holding mechanism includes inserting the dental cleaning device within the food accessory using an inserting mechanism.

According to an embodiment of the present invention, the holding mechanism includes placing the dental cleaning device on the food accessory at a specially designated location.

According to an embodiment of the present invention, the specially designated location on the food accessory includes a placeholder indicator indicating that the dental cleaning device can be placed in that location.

According to an embodiment of the present invention, the holding mechanism includes a special holding structure embedded on the food accessory that can hold the dental cleaning device.

According to an embodiment of the present invention, the holding mechanism includes embedding the dental cleaning device, either partially or completely, within the food accessory.

According to an embodiment of the present invention, the holding mechanism includes partially or completely affixing the dental cleaning device and the food accessory together.

According to an embodiment of the present invention, the holding mechanism includes any component or material, along with any shape or form, that can assist to hold the dental cleaning device and the food accessory together.

According to an embodiment of the present invention, the food accessory directly holds the dental cleaning device or the cover of the dental cleaning device using either temporary or permanent fastening or adhesive.

According to an embodiment of the present invention, the dental cleaning device has a clip mechanism on it such that the dental cleaning device can be attached to other objects.

According to an embodiment of the present invention, a food accessory that can hold a dental cleaning device comprising: a food accessory; and a holding apparatus on the food accessory that can hold a dental cleaning device.

According to an embodiment of the present invention, the holding apparatus includes an attachment affixed to the food accessory that is capable of holding a dental cleaning device either directly on it or using further embedded or attached components on it.

According to an embodiment of the present invention, the holding apparatus includes a special holding structure embedded on the food accessory to hold a dental cleaning device.

According to an embodiment of the present invention, the holding apparatus includes a specially designated location on the food accessory that can hold the dental cleaning device.

According to an embodiment of the present invention, the specially designated location on the food accessory includes a placeholder indicator indicating that the dental cleaning device can be placed in that location.

According to an embodiment of the present invention, the holding apparatus on the food accessory includes any component or material, along with any shape or form, that can assist to hold the dental cleaning device.

According to an embodiment of the present invention, the food accessory directly holds the dental cleaning device or the cover of the dental cleaning device using either temporary or permanent fastening or adhesive.

According to an embodiment of the present invention, one of the examples of the food accessory that directly holds the dental cleaning device includes a piece of cutlery with the dental cleaning bristles permanently attached to its handle.

According to an embodiment of the present invention, the food accessory is molded around the dental cleaning device such that the dental cleaning device is partially or completely embedded within the food accessory.

According to an embodiment of the present invention, a dental cleaning device that can be held on a food accessory comprising: a dental cleaning device; and a holding apparatus on the dental cleaning device that enables the dental cleaning device to be held on the food accessory.

According to an embodiment of the present invention, the holding apparatus includes an attachment affixed to the dental cleaning device that enables the dental cleaning device to be held on to the food accessory.

According to an embodiment of the present invention, the dental cleaning device or the cover of the dental cleaning device directly attaches to the food accessory using either temporary or permanent fastening or adhesive.

According to an embodiment of the present invention, the holding apparatus includes any component or material, along with any shape or form, that enables the dental cleaning device to be held on to the food accessory.

According to an embodiment of the present invention, the dental cleaning device includes multiple layers of its handle such that any of those handle layers can be removed or added back to the dental cleaning device.

According to an embodiment of the present invention, the dental cleaning device is partially or completely covered with mouth freshener.

DEFINITION/EXPLANATION OF KEY TERMS

A dental cleaning device can be any device that can be used to clean the teeth and/or gums, regardless of its size, material or shape. Here are some examples of dental cleaning devices—conventional toothbrush, automated toothbrush, finger toothbrush, foldable toothbrush, one-time use toothbrush, dental floss, mouthwash, cleaning bristles, dental cleaning twig, chewing stick, dental probiotic capsules, etc. A person of ordinary skill in the art would recognize that instead of the above examples any device that can clean the teeth and/or gums can also be used without departing from the spirit and scope of the present invention.

Food utensils can be any type of vessel or utensil where food is usually placed for consumption, regardless of their size, material or shape. For example, a food utensil material can include ceramic, plastic, paper, foam, metal, glass, or any other type of material. Here are some examples of food utensils—crockery, plates, cups, bowls, mugs, glasses, pans, earthenware, etc. A person of ordinary skill in the art would recognize that instead of the above examples any vessel or utensil that can hold food for consumption can also be used without departing from the spirit and scope of the present invention.

Food containers can be any type of containers that can store food products regardless of their size, material or shape. For example, a food container material can include either plastic, paper, foam, metal, glass, or any other type of material. Here are some examples of the food containers—boxes, wraps, packets, pouches, cans, bottles, etc. A person of ordinary skill in the art would recognize that instead of the above examples any food container that can store food can also be used without departing from the spirit and scope of the present invention.

Food accessories can be a variety of products where food may or may not be placed in those accessories, but those accessories are usually directly or indirectly involved with the foods and drinks and can sometimes even be decorative in nature. (Note: Such food accessories can be of any size, material or shape.) For example: serving utensils, cutlery/silverware such as knife, fork, spoon, etc., food utensil holders, cutlery holders, dining table mats, dining table linen, dining table centerpiece, dining table decorative items, paper napkins, table napkins, table cover, etc. A person of ordinary skill in the art would recognize that instead of the above examples any food accessories that are directly or indirectly involved with foods can also be used without departing from the spirit and scope of the present invention.

Bags used for carrying foods, food containers or food accessories can be any type of bags regardless of their size, material or shape. Here are some examples of such bags—plastic or paper bag, handbag, purse, luggage bag, laptop bag, etc. A person of ordinary skill in the art would recognize that instead of the above examples any bag that can carry foods, food containers or food accessories can also be used without departing from the spirit and scope of the present invention.

Food products can be either solid, semi-solid, liquid or any other type of foods or beverages that are edible. This would also include any foods/drinks that need to be prepared (for example: boiled, baked, fried, cooked, etc.) before consumption. Here are some examples of food products—an ice cream, an ice popsicle, kabab on sticks, a lollipop, or any breakfast, lunch, or dinner foods, etc. A person of ordinary skill in the art would recognize that instead of the above examples any other food can also be used without departing from the spirit and scope of the present invention.

A person of ordinary skill in the art would recognize that when the dental cleaning device is held on a food accessory, the meaning of 'held' can include either being attached, affixed, inserted, placed, embedded, molded, suspended, glued, fastened, secured, stuck, fixed, pinned, included, put, added, positioned, rooted in, set in, implanted, etc.

BRIEF DESCRIPTION OF THE DRAWINGS

FIG. 13 illustrates an exemplary dental cleaning device, a conventional toothbrush with a cover for keeping bristles clean, attached to an exemplary food container, a carry out rectangular box, using a tape.

FIG. 14 illustrates an exemplary food container, a lunch box with a special compartment to hold an exemplary dental cleaning device, a conventional toothbrush with a cover for keeping bristles clean, and an exemplary dental cleaning accessory, a toothpaste.

FIG. 15 illustrates an exemplary food container, a box, with a built-in compartment to hold an exemplary dental cleaning device, a conventional toothbrush, using magnet that's affixed to both the exemplary food container and the exemplary dental cleaning device. (Note: when one of the exemplary food container or the exemplary dental cleaning device is completely or partially made of ferrous components like iron, cobalt, nickel, etc, then the magnet would just need to be affixed to the remaining food container or the dental cleaning device since the magnet would attract to the ferrous objects.) Additionally, as shown in the figure, there can also an exemplary placeholder indicator on the box, indicating the specially allocated dental cleaning device section.

FIG. 16 illustrates an exemplary dental cleaning device, a dental floss within its protective case and covered in a plastic wrap, that's inserted in a pouch attached to an exemplary food container, a box of cookies. In addition, the figure also illustrates an exemplary dental cleaning device, a conventional toothbrush, attached to the flap/cover/lid of the food container using an attachment (for example: a tape). This figure demonstrates how the dental cleaning devices can be attached or inserted at prominent locations of the food container.

FIG. 17 illustrates an exemplary dental cleaning device, a conventional toothbrush covered in a plastic wrap, and suspended/inserted in an exemplary food container, i.e. a big packet of chocolates using a suspender that's attached (for example: glued) to the food container on one of its sides and attached (for example: glued) to the dental cleaning device (or its cover) on the other side.

FIG. 18 illustrates an exemplary dental cleaning device, a foldable toothbrush with a magnet on its handle, which allows it to be attached to an exemplary metal food container, an iron box.

FIG. 19 illustrates an exemplary food container, a bottle with an attachment, which can hold an exemplary dental cleaning device, a conventional toothbrush.

FIG. 20 illustrates an exemplary food container, a box of chocolates, with a special compartment to hold exemplary dental cleaning device, i.e. a dental floss, wherein the dental floss case is affixed to the said special compartment of the box using an adhesive.

FIG. 21 illustrates an exemplary food container, a big plastic packet of chocolates, which has a separate section to hold exemplary dental cleaning devices, i.e. multiple Y shaped dental flosses. In addition, there is also a separate cover for opening the dental cleaning devices' section.

DETAILED DESCRIPTION

Figures 1, 2:
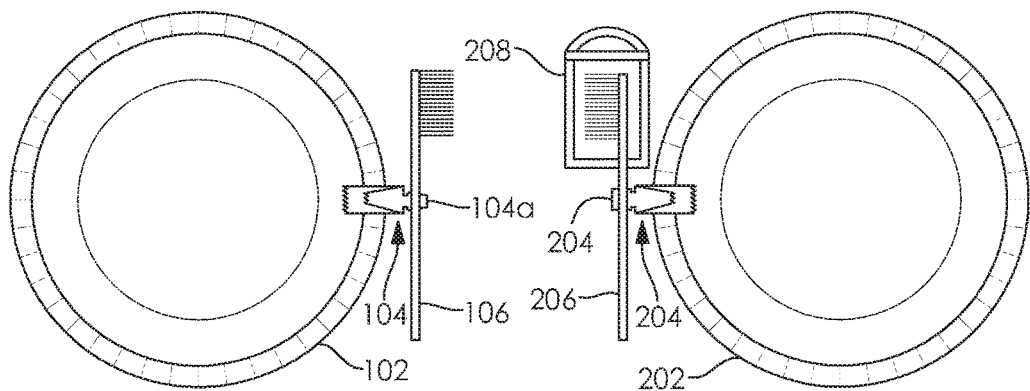
FIG. 1 illustrates an exemplary dental cleaning device, a conventional toothbrush, attached to an exemplary food utensil, a plate, using an attachment.
FIG. 2 illustrates an exemplary dental cleaning device, a conventional toothbrush with a cover for keeping bristles clean, attached to an exemplary food utensil, a plate, using an attachment.

This solution demonstrates a mechanism and exemplary apparatus to hold (for example: attach, affix, insert, place, embed, etc.) a dental cleaning device on food accessories such as food utensils, food containers, food accessories, bags used for carrying foods, food containers or food accessories, food products themselves, etc. This solution will not only make the dental cleaning devices easily accessible to users i.e. either right next to or on the food accessories themselves, but also provide a visual reminder to those users so they can frequently clean their teeth or gums, and therefore, avoid a lot of dental problems and their associated expenses. In short, whether it's children or adults, this solution of making the dental cleaning devices available right next to or on food accessories will promote and inculcate good habits of frequently cleaning the teeth or gums, and therefore, help to maintain good oral hygiene in the long run. The term "food" used throughout this application shall include both food and drink or beverages, consistent with the commonly understood, expansive meaning of food.

This solution would mainly include a dental cleaning device and a food accessory. Additionally, in situations where a dental cleaning device is attached to the food accessory, this solution can also include a built-in or add-on attachment to attach the dental cleaning device to the food accessory. Additionally, in situations where a dental cleaning device is inserted or placed on the food accessory, this solution can also include a placeholder indicator on the food accessory to indicate that the specially designated section has been allocated for keeping the dental cleaning devices. Moreover, when a dental cleaning device is inserted within a food accessory, this solution can also include an inserting mechanism, which would help to hold the dental cleaning device within that food accessory. Additionally, to protect the bristles and/or protect the entire dental cleaning device, this solution can also include a cover for either a part of or the entire dental cleaning device.

In one embodiment, the attachment device has a clip at one end that attaches to a food accessory and a flexible rubber claw at an opposite end, such that a dental cleaning device can be pressed inside the rubber claw. Another example of an attachment device can be an independent clip that is affixed (for example: attached, glued, embedded, etc.) to a dental cleaning device on one side, and using that clip the dental cleaning device can be attached to a food accessory. Another example of an attachment device can be a partial clip having one arm and spring mechanism attached to the dental cleaning device such that the base of the dental cleaning device acts as the other arm of the clip, allowing the dental cleaning device to be attached to a food accessory. Another example of an attachment device can be a solid material with hole in the center that can hold a dental cleaning device, and that solid material is affixed (for example: attached, glued, etc.) to the food accessory on one side. Another example of an attachment device can be a wire that is attached to a dental cleaning device on one side, and a food accessory on the other side. Another example of an attachment device can be a plastic cover that can hold the dental cleaning device within it and is attached to the food accessory. Another example of an attachment device can be a magnet that is either attached or embedded in a dental cleaning device, allowing the cleaning device to stick to food accessories that can attract magnets.

The attachment mentioned above can also have self-contained means so it can be readily secured to the food accessories, or the dental cleaning device itself without any external support. For example, the connecting end of the attachment device can be a clip with a groove which allows it to be attached to various food accessories.

Additionally, the attachment device mentioned above can also be dishwasher safe.

For those embodiments of the present invention where a dental cleaning device is attached to a food accessory using an attachment device, those dental cleaning devices would be detachable.

For those embodiments of the present invention where a dental cleaning device is any type of toothbrush with bristles, the material used for the handle of the toothbrush, the bristles or any other part of the toothbrush along with its cover would all be dishwasher safe, so the toothbrush can be placed in a dishwasher after usage. For those embodiments of the present invention where a dental cleaning device is placed on a food accessory, there can be either an embossed or debossed placeholder image of the dental cleaning device or placeholder text referring to the dental cleaning device on the food accessory, showing that a dental cleaning device can be placed in that specially designated section of the food accessory. The placeholder can also be an image or text (which aren't embossed or debossed) or another feature as long as it conveys the intent of placing a dental cleaning device on the particular section of the food accessory. Such placeholders would also provide a visual reminder to users that a dental cleaning device can be placed in those assigned sections. A person of ordinary skill in the art would recognize that such placement of dental cleaning device isn't limited to any of the exemplary details mentioned above and can also include other components, combinations and features that can convey the intent of placing a dental cleaning device in a particular section of the food accessory without departing from the spirit and scope of the present invention.

For those embodiments of the present invention where a dental cleaning device is held on a food accessory, a person of ordinary skill in the art would recognize that multiple dental cleaning devices can be held on a food accessory without departing from the spirit and scope of the present invention.

For those embodiments of the present invention where multiple dental cleaning devices are held on a food accessory, a person of ordinary skill in the art would recognize that each dental cleaning device can have a different color so that those users who might not be willing to share their dental cleaning devices with others can have a specific colored dental cleaning device assigned to them, and that would be within the spirit and scope of the present invention.

Several Exemplary Embodiments of the Present Disclosure are Described Herein Below with Reference to the Accompanying Drawings These exemplary embodiments demonstrate how a dental cleaning device can be held on a food accessory. However, it is to be clearly understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Note: A person of ordinary skill in the art would recognize that there are many different types of dental cleaning devices, food utensils, food containers, food accessories, bags used for carrying foods or food containers or food accessories, and the food products themselves, etc. Therefore, rather than limiting the invention to just the embodiments shown in this document, it is to be clearly understood that all other dental cleaning devices, food utensils, food containers, food accessories, bags used for carrying foods or food containers or food accessories, food products themselves, etc. would also be within the spirit and scope of the present invention.

Additionally, a person of ordinary skill in the art would recognize that any of the illustrated figures of this invention can also have substitute components, combinations and features as long as the intent of holding a dental cleaning device on the food accessory is maintained.

Additionally, a person of ordinary skill in the art would recognize that anywhere in this document that describes the dental cleaning device as being held on the food accessory, the meaning of 'held' can include being attached, affixed, inserted, placed, embedded, molded, suspended, glued, fastened, secured, stuck, fixed, pinned, included, put, added, positioned, rooted in, set in, implanted, etc., and all of these can be used interchangeably within the entire document without limiting their usage for a specific embodiment. (For example: if an embodiment of the present invention refers to a dental cleaning device being attached to a food accessory, then instead of being attached, the dental cleaning device can also be inserted, placed, embedded, molded, suspended, glued, fastened, secured, stuck, fixed, pinned, included, put, added, positioned, rooted in, set in, implanted, etc. on the food accessory, and that would be within the spirit and scope of the present invention.) Also, A person of ordinary skill in the art would also recognize that in addition to the above examples of 'held', any other meanings of 'held' would also be considered within the spirit and scope of the present invention.

According to an embodiment of the present invention, as shown in FIG. 1, an exemplary dental cleaning device in the form of a conventional toothbrush 106 is shown attached to an exemplary food utensil, a plate 102, using an attachment 104. The exemplary attachment 104 includes a clip like structure with grooves on the attaching end, which helps to secure it to the rim of the plate, and the other end of the clip includes a claw shaped rubber structure into which a dental cleaning device can be pressed.

This embodiment shown in FIG. 1 is just exemplary, however, it shows how a dental cleaning device can be easily attached to the food accessories, providing a visual reminder to users to frequently clean their teeth or gums and also making the dental cleaning device easily accessible. This easy access can encourage users to frequently clean their teeth or gums, and therefore, avoid a lot of dental problems and their associated expenses. Please note that the dental cleaning device shown in the exemplary embodiment is detachable and re-attachable from the food accessory.

According to an embodiment of the present invention, as shown in FIG. 2, an exemplary dental cleaning device in the form of a conventional toothbrush 206 is shown with a cover 208 for keeping bristles clean. The dental cleaning device is attached to an exemplary food utensil, a plate 202, using an attachment 204. Similar to the attachment 104 shown in FIG. 1, the exemplary attachment 204 includes a clip like structure with grooves on the attaching end, which helps to secure it to the rim of the plate, and the other end of the clip includes a claw shaped rubber structure into which a dental cleaning device can be pressed. In short, the primary intent of this FIG. 2 is to demonstrate that a cover 208 can also be used along with the dental cleaning device in order to keep it clean while the dental cleaning device is attached to a food accessory.

Figures 3, 4:
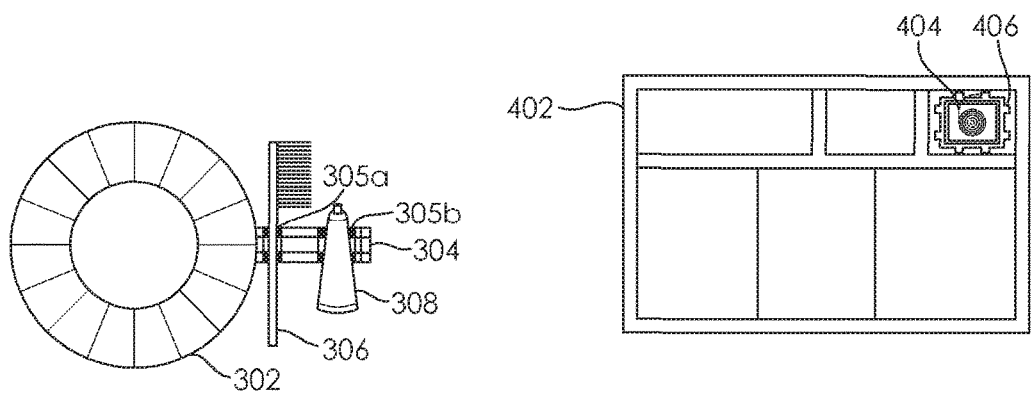
FIG. 3 illustrates an exemplary food utensil, a plate with a built-in extension to hold an exemplary dental cleaning device, a conventional toothbrush, and an exemplary dental cleaning accessory, a toothpaste.
FIG. 4 illustrates an exemplary food utensil, a plate, with a built-in compartment and an exemplary placeholder indicator to hold an exemplary dental cleaning device, a dental floss within its protective cover.

According to an embodiment of the present invention in FIG. 3 an exemplary food utensil in the form of a plate 302 is shown with a built-in extension i.e. a special holding structure 304 with retention slots 305a and 305b to hold an exemplary dental cleaning device, a conventional toothbrush 306, and an exemplary dental cleaning accessory, a toothpaste 308. Such extension 304 can be made of either the same material as the food utensil itself, or it can also be made of any other material as long as the material can be affixed to the food utensil and can hold the dental cleaning devices on it. Other components can be attached or embedded in the built-in extension 304 in order to hold dental cleaning devices. For example, there can be a claw shaped rubber structure embedded in the built-in extension 304, which would allow it to hold the dental cleaning devices along with the dental cleaning accessories. The built-in extension would be affixed or fastened to the food utensil such that the extension can be folded beneath, above or within the product itself after usage, and therefore, not take up additional space during storage.

According to an embodiment of the present invention in FIG. 4 an exemplary food utensil in the form of a plate 402 is shown, with a built-in compartment and an exemplary placeholder indicator 406 to hold an exemplary dental cleaning device, such as dental floss 404 within its protective cover. The exemplary placeholder indicator 406 used here includes a debossed image of floss which indicates that the dental cleaning device can be placed in that specially allocated section of the food accessory. Such exemplary placeholder indicators can be an embossed, debossed or placeholder image or text referring to a dental cleaning device, or it can also be another form of representation as long as it conveys the intent of placing a dental cleaning device on the particular section of food accessory. Such placeholders also serve as a visual reminder to users that a dental cleaning device can be placed in the assigned sections of the food accessory. However, the placeholder indicator is not required for the proper functioning of the invention.

Figures 5, 6:
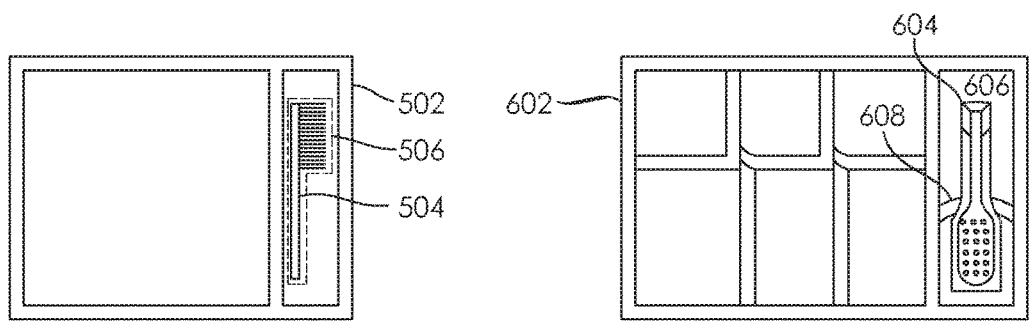
FIG. 5 illustrates an exemplary food utensil, a plate with a built-in compartment and an exemplary placeholder indicator to hold an exemplary dental cleaning device, a conventional toothbrush.
FIG. 6 illustrates an exemplary food utensil, a plate with a built-in compartment, an exemplary placeholder indicator and an exemplary holding unit to hold an exemplary dental cleaning device, a foldable toothbrush.

According to an embodiment of the present invention in FIG. 5, an exemplary food utensil in the form of a plate 502 is shown with a built-in compartment and an exemplary placeholder indicator 506 to hold an exemplary dental cleaning device, a conventional toothbrush 504. The exemplary placeholder indicator 506 used here includes an embossed outline of toothbrush. Similar to FIG. 4, the main intent of such placeholder indicators is to remind users that dental cleaning devices are important to maintain good oral health, and therefore, deserve a spot either within or right next to the food accessories. However, the placeholder indicators need not be present.

According to an embodiment of the present invention in FIG. 6, an exemplary food utensil in the form of a plate 602 is shown with a built-in compartment, an exemplary placeholder indicator 606, and a holding unit 608 to hold an exemplary dental cleaning device, a foldable toothbrush 604. The exemplary placeholder indicator 606 used here includes an embossed text referring to a dental cleaning device, which indicates that the cleaning device can be placed in that specially designated section of the food accessory. However, the placeholder indicators need not be present. In addition, the holding unit 608 shown in this embodiment can be made of either the same material as the food utensil itself, or it can also be made of any other material as long as the material can be affixed to the food utensil and can hold the dental cleaning device.

Figure 7:
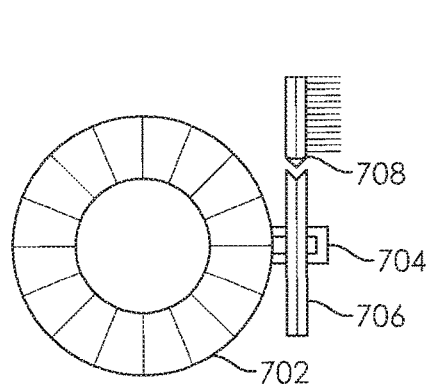
FIG. 7 illustrates an exemplary food utensil, a plate with a built-in extension to hold an exemplary dental cleaning device, a toothbrush with replaceable front bristles.

According to an embodiment of the present invention in FIG. 7, an exemplary food utensil in the form of a plate 702 is shown with a built-in extension i.e. a special holding structure 704 to hold an exemplary dental cleaning device, such as a toothbrush 706 with replaceable front bristles 708. This toothbrush is similar to the use-and-throw concept, where once a user has used the toothbrush, they can take out the front bristles section and replace it with another one. The built-in extension 704 illustrated in FIG. 7 can be made of either the same material as the food utensil itself, or it can also be made of any other material as long as the material can be affixed to the food utensil and can hold the dental cleaning devices on it. Other components can also be attached or embedded on the built-in extension 704 to hold dental cleaning devices. For example, there can be a claw shaped rubber structure that's embedded in the built-in extension 704, which would allow it to hold the dental cleaning devices. The built-in extension would be affixed or fastened to the food utensil such that the extension can be folded beneath, above or within the product itself after usage, and therefore, not take up additional space during storage. Additionally, A person of ordinary skill in the art would recognize that such toothbrush with replaceable front bristles, as illustrated in the figure, can also exist separately on its own such that it can also be inserted, embedded or placed on a food accessory without departing from the spirit and scope of the present invention.

Figure 8:
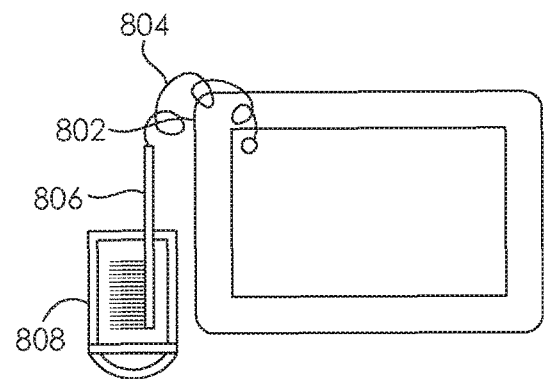
FIG. 8 illustrates an exemplary food utensil, a plate with an attached wire that connects the plate and an exemplary dental cleaning device, a conventional toothbrush with a cover for keeping bristles clean.

According to an embodiment of the present invention in FIG. 8, an exemplary food utensil in the form of a plate 802 is shown with an attached wire 804 that connects the plate and an exemplary dental cleaning device, a conventional toothbrush 806 with a cover 808 for keeping bristles clean. The exemplary wire 804 can be either affixed to the food related accessory as well as the dental cleaning device, or there can be a hole on the food related accessory as well as the dental cleaning device where the wire can be fastened on both sides. In addition, there can be also be a combination of wire being affixed, fastened to holes or other potential means can also be used to attach the wire to the food accessory as well as the dental cleaning device without restricting it to the examples mentioned above.

Figure 9:
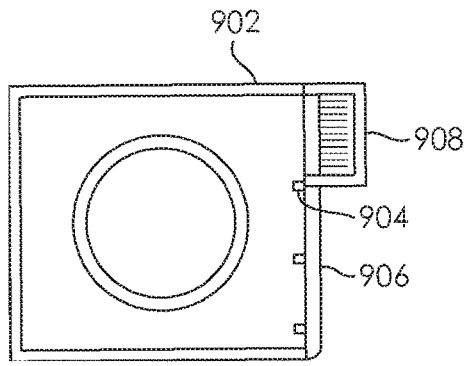
FIG. 9 illustrates an exemplary food utensil, a disposable plate, with an attached exemplary dental cleaning device, a conventional toothbrush that can be snapped out of the utensil.

According to an embodiment of the present invention in FIG. 9, an exemplary food utensil in the form of a disposable plate 902 is shown, with an attached exemplary dental cleaning device, a conventional toothbrush 906 that can be snapped out of the utensil when the user wishes to clean their teeth or gums. As shown in the figure, the spine of the toothbrush is attached to one side of the disposable plate at certain key points 904, so the toothbrush can be easily snapped out of the utensil. However, please note that the toothbrush can be attached in a number of other ways without restricting it to the example mentioned above. Additionally, the conventional toothbrush in the figure also has a cover 908 for keeping bristles clean, however, the cover is just for good hygiene purposes and isn't necessary.

Figure 10:
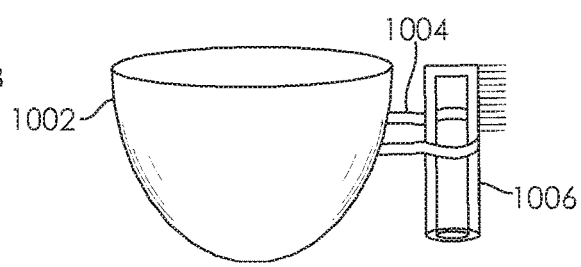
FIG. 10 illustrates an exemplary food utensil, a bowl with a built-in extension to hold an exemplary dental cleaning device, a finger toothbrush.

According to an embodiment of the present invention in FIG. 10, an exemplary food utensil in the form of a bowl 1002 is shown with a built-in extension 1004 to hold an exemplary dental cleaning device, a finger toothbrush 1006. As illustrated in the figure, the built-in extension 1004 includes a hole on one of its ends, which can hold a dental cleaning device in it, and the other end is affixed to the food accessory. The built-in extension 1004 can be made of either the same material as the food utensil itself, or it can also be made of any other material as long as the material can be affixed to the food utensil and can hold the dental cleaning devices on it. If needed, other components can also be attached or embedded on the built-in extension 1004 to hold the dental cleaning devices. The built-in extension would be affixed or fastened to the food utensil such that the extension can be folded beneath, above or within the product itself after usage, and therefore, not take up additional space during storage.

Figure 11:
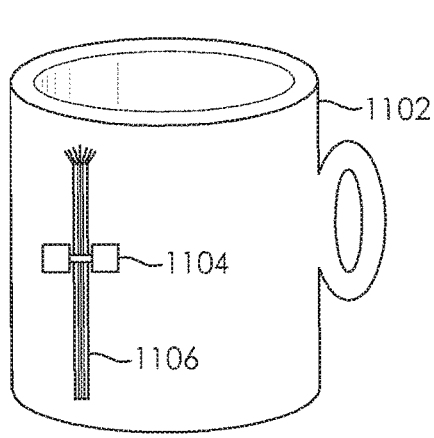
FIG. 11 illustrates an exemplary food utensil, a mug with a built-in holding unit to hold an exemplary dental cleaning device, a teeth cleaning chewing stick.

According to an embodiment of the present invention in FIG. 11, an exemplary food utensil in the form of a mug 1102 is shown with a built-in holding unit 1104 to hold an exemplary dental cleaning device, a teeth or gum cleaning chewing stick 1106. The built-in holding unit 1104 (i.e. a special holding structure) illustrated in the figure can be made of either the same material as the food utensil itself, or it can also be made of any other material as long as the material can be affixed to the food utensil and can hold the dental cleaning devices on it. For example, a claw shaped rubber structure can serve as a holding unit 1104, which would be affixed to the food utensil and would hold the dental cleaning device. Other components can also be attached to or embedded in the built-in holding unit 1104 to hold the dental cleaning devices. A person of ordinary skill in the art would recognize that such holding unit 1104 isn't limited to any of the exemplary details mentioned above and can also include other components, combinations and features that can hold the dental cleaning device on the food accessory without departing from the spirit and scope of the present invention. Additionally, the teeth or gum chewing stick shown in FIG. 11 can be replaced with a toothbrush or another type of dental cleaning device without departing from the spirit and scope of the present invention. In short, any of the illustrated figures of this invention can have substitute components, combinations and features as long as the intent of holding a dental cleaning device on the food accessory is maintained.

Figure 12:
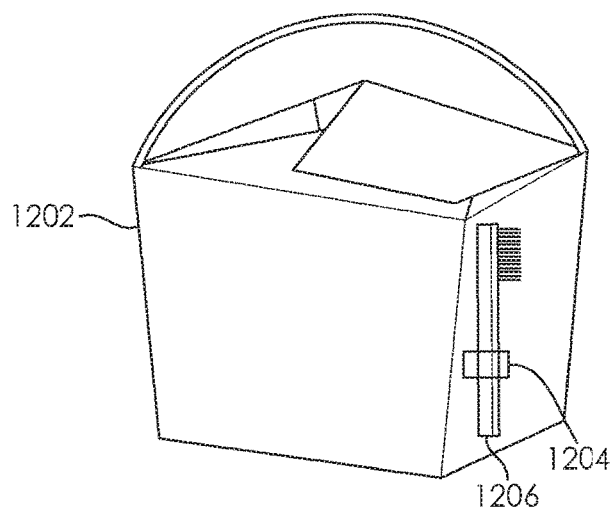
FIG. 12 illustrates an exemplary dental cleaning device, a conventional toothbrush, attached to an exemplary food container, a carry out box, using an attachment.

According to an embodiment of the present invention in FIG. 12, an exemplary dental cleaning device in the form of a conventional toothbrush 1206 is shown attached to an exemplary food container, a carry out box 1202, using a sticky back strip or hold down strip (For example: Velcro products) 1204. The sticky back strip 1204 would be fastened to both the food container as well as the dental cleaning device, which would allow those two products to attach together using the Velcro strip component. Even a simple tape or another sticking or attaching component can be used instead of a Velcro sticky back strip to attach the dental cleaning device to the food container without departing from the spirit and scope of the present invention. In addition, even multiple dental cleaning devices can also be attached to a single food container without departing from the spirit and scope of the present invention.

According to an embodiment of the present invention in FIG. 13, an exemplary dental cleaning device in the form of a conventional toothbrush 1306 is shown with a cover 1308 for keeping bristles clean, attached to an exemplary food container, a carry out rectangular box 1302, using a tape 1304. A Velcro sticky back strip or a similar sticking or attaching material can be used instead of tape to attach the dental cleaning device to the food container without departing from the spirit and scope of the present invention. In addition, multiple dental cleaning devices can also be attached to a single food container without departing from the spirit and scope of the present invention.

According to an embodiment of the present invention in FIG. 14, an exemplary food container in the form of a lunch box 1402 is shown with a special compartment 1404 to hold an exemplary dental cleaning device, a conventional toothbrush 1406 with a cover 1408 for keeping bristles clean, and an exemplary dental cleaning accessory, a toothpaste 1410. The special compartment on the lunch box can also include an exemplary placeholder indicator (for example: text referring to dental cleaning section), which would indicate and remind users that the dental cleaning devices can be kept in that specially designated section of the food accessory. However, the placeholder indicators need not be present.

According to an embodiment of the present invention in FIG. 15, an exemplary food container in the form of a box 1502 is shown with a built-in special compartment 1504 to hold an exemplary dental cleaning device, a conventional toothbrush 1506, using magnet 1510 that's affixed to both the exemplary food container and the exemplary dental cleaning device. A person of ordinary skill in the art would recognize that when one of the exemplary food container or the exemplary dental cleaning device is completely or partially made of ferrous components like iron, cobalt, nickel, etc, then the magnet 1510 would just need to be affixed to the food container or the dental cleaning device since the magnet would be attracted to the ferrous objects, and that would be within the spirit and scope of the present invention. In addition, the magnet 1510 can either be visibly located outside or embedded inside (invisible from outside) the exemplary dental cleaning device or the exemplary food container, and that would also be within the spirit and scope of the present invention. Whether the magnet 1510 is located outside or embedded inside the dental cleaning device or food container, it would still be able to maintain its magnetic field. In addition, as shown in the figure, the special compartment 1504 on the box can also include an exemplary placeholder indicator 1508 (for example: an outline of a toothbrush), which would indicate and remind users that the dental cleaning devices can be kept in that specially designated section of the food accessory. The main intent of such special compartments or placeholder indicators is to remind users that dental cleaning devices are important to maintain good oral health. However, the placeholder indicators need not be present.

According to an embodiment of the present invention in FIG. 16 an exemplary dental cleaning device in the form of a dental floss 1604 is shown within its protective case 1606 and covered in a plastic wrap 1608, that's inserted in a pouch 1610 attached to an exemplary food container, a box of cookies 1602. The pouch 1610 can be made of plastic, paper or any other material as long as it can be affixed (for example: glued) to the food container and can hold the dental cleaning device in it. The pouch 1610 can be similar to a computer CD case in which items can be inserted and which can also be affixed to a food container. In addition to the pouch detailed above, the figure also illustrates an exemplary dental cleaning device, a conventional toothbrush 1612, attached to the lid 1616 of the food container 1602 using an attachment means 1614 such as tape. The attachment means 1614 can also include other materials as long as they attach the dental cleaning device to the food container, and that would also be within the spirit and scope of the present invention. By attaching or inserting the dental cleaning devices at such prominent locations as shown in FIG. 16, it's clear that this invention would provide a reminder to users to frequently clean their teeth or gums whenever they open the food container.

Additionally, as illustrated in FIG. 16, a person of ordinary skill in the art would recognize that the intent of covering the dental cleaning device in plastic wrap 1608 or a similar wrap is not only to protect the dental cleaning device but also to clearly distinguish the dental cleaning device from the other contents of the food container. However, the wrap is not a required component of the invention. Also, it is to be clearly understood that even a different food container like a cereal box, box of snacks, etc. would also be a valid example under this invention as long as a dental cleaning device can be held on the food accessory.

According to an embodiment of the present invention in FIG. 17, an exemplary dental cleaning device in the form of a conventional toothbrush 1704 is shown covered in a plastic wrap 1706, and inserted in an exemplary food container, i.e. a big packet of chocolates 1702, using a suspender 1708 that's attached 1710 (for example: glued) to the food container on one of its sides and attached 1712 (for example: glued) to the dental cleaning device (or its cover) on the other side. Such suspender 1708 can be made of any material and can have any shape as long as it can be affixed to the food container and can act as an inserting mechanism i.e. suspend the dental cleaning device within or outside the food container. A person of ordinary skill in the art would recognize that the intent of covering the dental cleaning device in plastic wrap 1706 or a similar wrap is to protect the dental cleaning device and also to clearly distinguish the dental cleaning device from the other contents of the food container. However, the wrap is not a necessary component of the invention. A person of ordinary skill in the art would also recognize that multiple dental cleaning devices can also be suspended, inserted, placed, embedded or attached to a single food container.

According to an embodiment of the present invention in FIG. 18 an exemplary dental cleaning device in the form of a foldable toothbrush 1806 is shown with a magnet 1804 on its handle, which allows it to be attached to an exemplary metal food container, an iron box 1802. The magnet 1804 on the toothbrush can either be visibly located outside on the toothbrush handle or it can also be embedded inside (invisible from outside) within the handle of the toothbrush, however, in either case the magnet 1804 would still be able to maintain its magnetic field. Since a magnet usually attracts to ferrous objects like iron, cobalt, nickel, etc. or is attracted to another magnet with opposite polarity. A person of ordinary skill in the art would recognize that even those food accessories that don't attract magnets can have a separate magnet affixed to them such that a dental cleaning device with magnet (of opposite magnetic pole) on its handle would be attracted to and attached to the food accessory. In short, a magnet can be used to attach a dental cleaning device to a food accessory. Additionally, a magnet can be affixed at any place on the toothbrush handle, however, it is preferably affixed near the end of the handle so that users don't put the magnet in their mouth while cleaning their teeth or gums.)

According to an embodiment of the present invention in FIG. 19, an exemplary food container in the form of a bottle 1902 is shown with an attachment 1904, which can hold an exemplary dental cleaning device, a conventional toothbrush 1906. This figure demonstrates how a user can even attach a dental cleaning device to drink accessories. The attachment 1904 illustrated in the figure includes a round material with hole in the center, which can hold a dental cleaning device like a toothbrush, and that attachment is affixed (for example: glued) to the food container, i.e. a bottle, on one side. The attachment 1904 can be made of any material and can have any shape as long as it can attach to or hold the dental cleaning device. A person of ordinary skill in the art would recognize that the dental cleaning device can even have a suction cup like attachment on it, which allows the dental cleaning device to be attached to an exemplary food container or utensil. Also, if the suction cup like attachment is affixed to the food container or utensil, then that would also allow the dental cleaning device to be attached to the suction cup attachment, and therefore to the food container or utensil.

According to an embodiment of the present invention in FIG. 20 an exemplary food container in the form of a box of chocolates 2002 is shown with a special compartment 2004 to hold the exemplary dental cleaning device, i.e. a dental floss 2006. The dental floss case is affixed to the special compartment 2004 of the box using an adhesive 2008. This embodiment would allow users who consume the chocolates to pull out the floss directly from the dental floss case that's affixed to the chocolate box. The special compartment 2004 of the box can also include an exemplary placeholder indicator, which indicate or reminds users that the special compartment is allocated for the dental cleaning devices. A person of ordinary skill in the art would also recognize that rather than inserting the dental cleaning devices in the special compartment of the box, the dental cleaning devices can also be attached to any other place on the box. For example, the dental cleaning device can be attached to an exterior or interior rim of the box, a cover of the box, or some other part of the box.

According to an embodiment of the present invention in FIG. 21, an exemplary food container in the form of a big plastic packet of chocolates 2102 is shown, which has a separate section 2104 to hold exemplary dental cleaning devices, i.e. multiple Y shaped dental flosses 2106. In addition, the embodiment also includes a separate cover 2108 for opening the dental cleaning devices' section. In short, this arrangement allows the chocolates and the dental cleaning devices to be placed in completely separate sections with separate covers for opening those sections, however, everything still resides within one big packet. There can also be placeholder indicators on the dental cleaning devices' section of the box, which indicate or remind users that the separate section is allocated specially for the dental cleaning devices.

Figure 22:
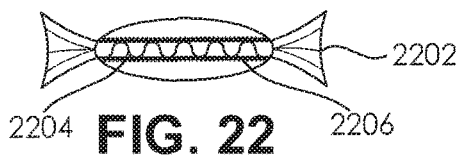
FIG. 22 illustrates an exemplary food container, a chocolate wrapper, with an attached exemplary dental cleaning device, a dental floss within a cover, surrounding the outer wall of the wrapper.

According to an embodiment of the present invention in FIG. 22, an exemplary food container in the form of a chocolate wrapper 2202 is shown with an attached exemplary dental cleaning device, a dental floss 2204 within a cover 2206, surrounding the outer wall of the wrapper. As illustrated, the dental floss within its cover is attached using a glue (for example: temporary adhesive that produces a non-permanent joint) to the chocolate wrapper, however, even a tape, booger glue, gooey glue, Velcro sticky back strip or a similar sticking or holding material can be used to attach the dental cleaning device to the food container without departing from the spirit and scope of the present invention. Overall, this illustration shows how the individual food items or accessories like an individual chocolate wrapper 2202 can have a dental cleaning device like a floss 2204 attached to them. This would not only provide users with easy access to dental cleaning devices but also remind users to clean their teeth or gums after they have consumed their foods.

A person of ordinary skill in the art would recognize that a dental cleaning device, for example: a floss, can be attached to food accessories, for example: a chocolate wrapper, at any place (internally or externally) and in any form or pattern. (For example, a floss can also be attached in a rounded pattern at the corner points where the chocolate wrapper is usually folded, etc.) A person of ordinary skill in the art would also recognize that a dental cleaning device, such as dental floss, can be attached to a food container, such as a chocolate wrapper, either directly or within a protective cover, and either of those would still be within the spirit and scope of the present invention. Additionally, A person of ordinary skill in the art would also recognize that a dental cleaning device, such as dental floss, can also be embedded in the food container, so that once a user is done eating the food item the user can just snap out or pull out the floss from the wrapper and use it for cleaning their teeth or gums.

Figure 23:
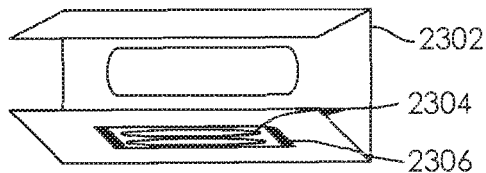
FIG. 23 illustrates an exemplary food container, an open chocolate wrapper, with an attached exemplary dental cleaning device, a dental floss within a cover, located within multiple folds of the inner wall of the wrapper.

According to an embodiment of the present invention in FIG. 23, an exemplary food container in the form of an open chocolate wrapper 2302 is shown with an attached exemplary dental cleaning device, a dental floss 2304 within a cover 2306, located within multiple folds of the inner wall of the wrapper. In this example, a dental floss 2304 within its cover 2306 is first wrapped within a couple of small folds of one end of the chocolate wrapper, and the remaining wrapper is used to wrap the chocolate. Using this method, both the chocolate and the floss can co-exist in the same wrapper, however, the folds of the wrapper form a separation between them. In short, if the user unwraps the chocolate wrapper they would first see the chocolate, and then if they unfold the remaining folds that are present on one side of the chocolate wrapper, they would also see the dental cleaning device i.e. a floss, either with or without its covering.

Figure 24:
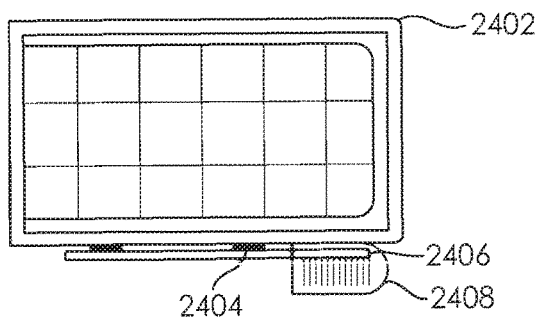
FIG. 24 illustrates an exemplary food container, a packet of chocolate bar, with an attached exemplary dental cleaning device, a conventional toothbrush with a cover for keeping bristles clean. The attachment illustrated in the figure is that of a booger glue or E-Z-Release glue, which provides temporary adhesiveness and helps to attach the dental cleaning device to the food container i.e. a packet of chocolate bar.

According to an embodiment of the present invention in FIG. 24, an exemplary food container in the form of a packet of chocolate 2402 is shown with an attached exemplary dental cleaning device, a conventional toothbrush 2406 with a cover 2408 for keeping bristles clean. The attachment 2404 illustrated in the figure is that of a booger glue or E-Z-Release glue, which provides temporary adhesiveness and helps to attach the dental cleaning device to the food container i.e. a packet of chocolate. After eating some or all of the edible contents within the chocolate packet, a user can pull out the toothbrush from the packet to clean their teeth or gums. A person of ordinary skill in the art would recognize that instead of the above mentioned booger/E-Z-Release glue, other products which produce a removable, non-permanent joint, can be used without departing from the spirit and scope of the present invention. A person of ordinary skill in the art would also recognize that the dental cleaning device can be placed within a cover, and the cover can be attached to the food container without departing from the spirit and scope of the present invention.

Figure 25:
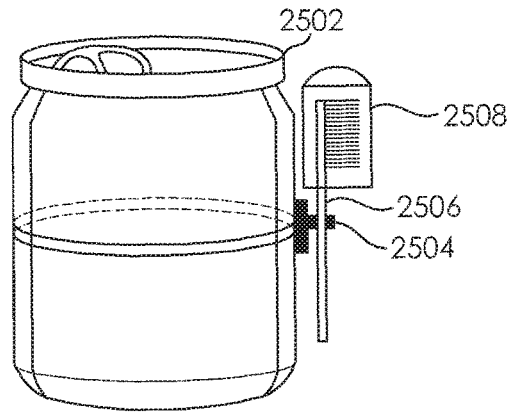
FIG. 25 illustrates an exemplary food container, a cylindrical metal can with an attachment to hold an exemplary dental cleaning device, a conventional toothbrush along with a cover to keep bristles clean.

According to an embodiment of the present invention in FIG. 25, an exemplary food container in the form of a cylindrical metal can 2502 is shown with an attachment 2504 to hold an exemplary dental cleaning device, a conventional toothbrush 2506 along with a cover 2508 to keep bristles clean. The attachment 2504 illustrated in the figure includes a round band that tightly fits the cylindrical metal can and has a claw shaped rubber structure on one of its sides, which can hold the dental cleaning device on it. The round band mentioned above can include any material as long as that material can be affixed to the food container and can hold the dental cleaning device on it. Other components can also be attached to or embedded in the attachment 2504 to hold the dental cleaning devices. A person of ordinary skill in the art would recognize that such attachment 2504 isn't limited to any of the exemplary details mentioned above and can also include other components, combinations and features that can hold the dental cleaning device on the food accessory without departing from the spirit and scope of the present invention.

Figure 26:
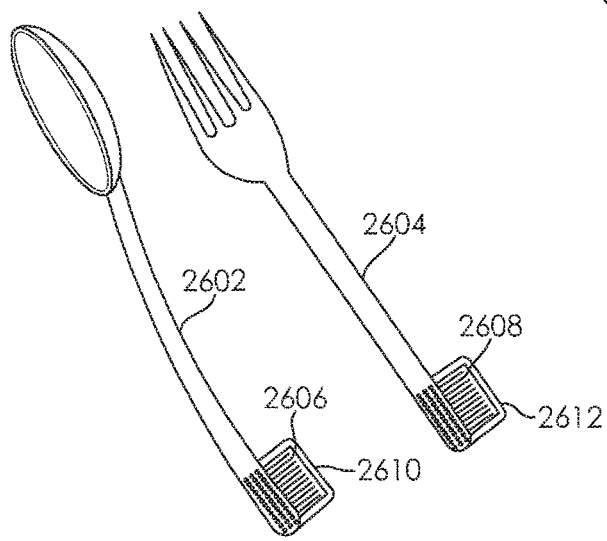
FIG. 26 illustrates exemplary food related accessory, a spoon and a fork, which have an exemplary dental cleaning device, i.e. bristles, embedded or attached at the back of the utensil handle, and the bristles have a cover in order to keep them clean.

According to an embodiment of the present invention in FIG. 26, an exemplary food related accessory in the form of a spoon 2602 is shown, which has an exemplary dental cleaning device, i.e. bristles 2606, embedded or attached at the back of the spoon's handle, and the bristles have cover 2610 in order to keep them clean. Similarly, FIG. 26 also illustrates another exemplary food related accessory, a fork 2604, which has an exemplary dental cleaning device, i.e. bristles 2608, embedded or attached at the back of the fork's handle, and the bristles have cover 2612 in order to keep them clean. In the above examples shown in FIG. 26, the bristles can also be embedded or attached to the utensil handle similar to how the bristles are embedded or attached on a conventional toothbrush. For example, bristles can be positioned into the holes created at the base of the utensil handle and then fastened with tiny staples or similar attaching process. In fact, any other embedding or attaching process would also be considered within the spirit and scope of the present invention as long as that process can embed or attach the bristles to the food accessories. After eating food with the above mentioned utensil, a user can simply remove the cover from the bristles and clean their teeth or gums with the other end of the utensil that has the embedded or attached bristles. A person of ordinary skill in the art would recognize that the covers 2610 and 2612 illustrated in the figure are used to keep bristles clean, however, the cover is for good hygiene purposes and isn't always necessary.

Figure 27:
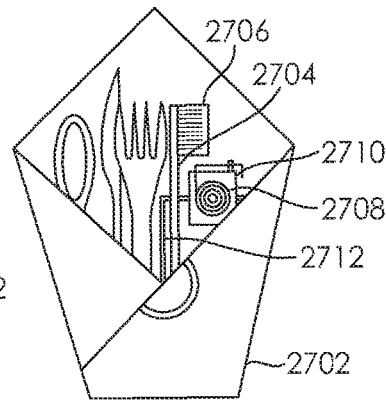
FIG. 27 illustrates exemplary dental cleaning devices, a conventional toothbrush and a dental floss within their respective covers, inserted within a separate section of an exemplary food related accessory, a folded table napkin, which also holds the conventional fork, knife, spoon, etc. within that same table napkin.

According to an embodiment of the present invention in FIG. 27, exemplary dental cleaning devices in the form of a conventional toothbrush 2704 and a dental floss 2708 are shown, within their respective covers 2706, 2710, inserted within a separate section 2712 of an exemplary food related accessory, a folded table napkin 2702. The folded table napkin 2702 is usually kept on the dining table along with other food accessories, but conventionally it only includes accessories that can help users to consume foods. However, based on this invention, the folded table napkin would also have a separate section 2712 affixed to it, which would hold the dental cleaning devices 2704, 2708. A person of ordinary skill in the art would recognize that the separate section on the table napkin can be either made of the same material as the table napkin itself or can also be made of any other material as long as it can hold dental cleaning devices in it.

Figure 28:
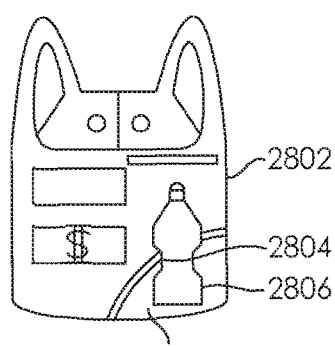
FIG. 28 illustrates an exemplary bag, i.e. a purse carrying either food, food container or food accessories, and includes a separate section that can hold the dental cleaning devices such as an antiseptic mouthwash, etc. Additionally, there is also an exemplary placeholder indicator on the purse i.e. text referring to the dental cleaning device section on the purse.

According to an embodiment of the present invention in FIG. 28 an exemplary bag, in the form of a purse 2802 is shown which includes a separate section 2804 that can hold a dental cleaning device such as an antiseptic mouthwash 2806, etc. Additionally, as illustrated in the figure, there is also an exemplary placeholder indicator 2808 (for example: text referring to the dental cleaning device section) on the purse, indicating or reminding users that the special compartment 2804 has been allocated to hold the dental cleaning device. Such placeholder indicators can also be in any other form (for example: image, bright light, embossed, debossed text, etc.) as long as they convey the intent of placing a dental cleaning device on the particular section of the food accessory.

Figure 29:
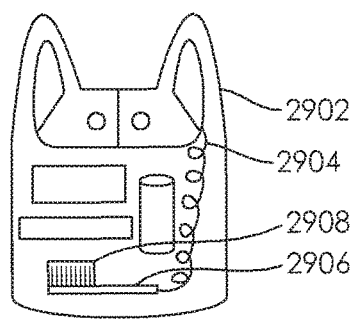
FIG. 29 illustrates an exemplary bag, i.e. a purse carrying either food, food container or food accessories, and also has a built-in wire connecting the bag and the exemplary dental cleaning device, a conventional toothbrush along with a cover to keep bristles clean.

According to an embodiment of the present invention in FIG. 29, an exemplary bag in the form of a purse 2902 is shown with a built-in wire 2904 connecting the bag and the exemplary dental cleaning device, a conventional toothbrush 2906 along with a cover 2908 to keep bristles clean. Such exemplary wire 2904 can be either affixed to the bag as well as the dental cleaning device, or there can be an attachment on the bag as well as the dental cleaning device where the wire can be fastened on both sides. In addition, a person of ordinary skill in the art would also recognize that there can also be a special section assigned in the purse where the dental cleaning devices can be held without departing from the spirit and scope of the present invention.

Figure 30:
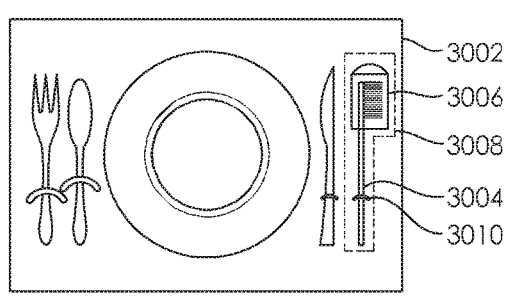
FIG. 30 illustrates an exemplary dental cleaning device, a conventional toothbrush, attached to an exemplary food related accessory, a dining table mat using an attachment. In addition, there is also an exemplary placeholder indicator on the dining table mat, indicating that the dental cleaning device can be kept on that special section of the dining table mat. Additionally, as illustrated in the figure, conventional toothbrush can also have a cover for keeping bristles clean.

According to an embodiment of the present invention in FIG. 30, an exemplary dental cleaning device in the form of a conventional toothbrush 3004 is shown attached to an exemplary food related accessory, a dining table mat 3002 using an attachment 3010. The attachment 3010 can be made of any material and can have any shape as long as it can hold the dental cleaning device. (For example: an attachment can be a small strip of plastic that's affixed on its ends to the dining table mat such that a small semi-circle with a hole is created and can hold a dental cleaning device in it.) In addition, as illustrated in the figure, there is also an exemplary placeholder indicator 3008 on the dining table mat 3002, indicating that the dental cleaning device 3004 can be kept on that special section of the dining table mat. In addition, as illustrated in the figure, toothbrush 3004 also has a cover 3006 to keep the bristles clean, however, note that such cover isn't always necessary. Additionally, as illustrated in this figure, the exemplary placeholder indicator 3008 includes an embossed outline of toothbrush. However, such exemplary placeholder indicators can either be embossed, debossed or even regular placeholder image or text referring to a dental cleaning device, or it can also be another form of representation as long as it conveys the intent of placing a dental cleaning device on the particular section of the food accessory. Such placeholder indicators 3008 also serve as a visual reminder for users that a dental cleaning device can be placed in the allocated section of the food accessory. Conventionally, only those accessories are placed on a dining table mat that can help the users to consume the foods. However, as illustrated in FIG. 30, it is to be clearly understood that a dental cleaning device 3004 is as important as other food accessories such as a fork, spoon, or knife, and therefore, they can also be attached to a food related accessory, such as a dining table mat.

Figure 31:
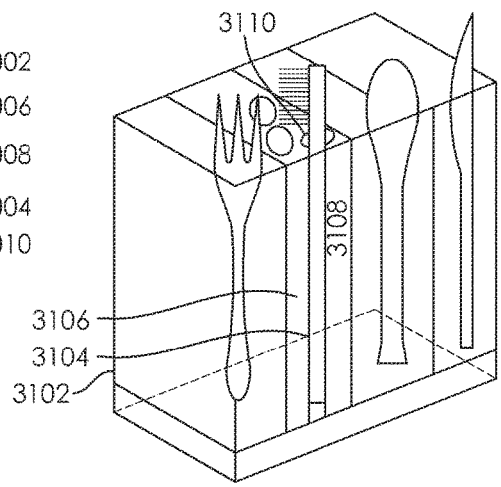
FIG. 31 illustrates an exemplary food related accessory, a cutlery holder, with a built-in compartment to also hold an exemplary dental cleaning device, a regular toothbrush, along with the conventional fork, knife, spoon, etc. Additionally, as illustrated in the figure, the dental cleaning device section of the cutlery holder can also include partition holes at the top, which would allow to keep the dental cleaning devices separate from each other and protect their bristles. In addition, the figure also illustrates an exemplary placeholder indicator on the cutlery holder, referring to the dental cleaning device section of the food related accessory.

According to an embodiment of the present invention in FIG. 31, an exemplary food related accessory in the form of a cutlery holder 3102, with a built-in special compartment 3106 to hold an exemplary dental cleaning device, a regular toothbrush 3104, along with the conventional fork, knife, spoon, etc. Additionally, as illustrated in the figure, the special compartment 3106 i.e. the dental cleaning device section of the cutlery holder 3102 can also include partition holes 3110 at the top, which would allow one to keep the dental cleaning devices 3104 separate from each other and protect their bristles. In addition, as illustrated in the figure, there is also an exemplary placeholder indicator 3108 (for example: text referring to the dental cleaning device) on the food related accessory, i.e. a cutlery holder, which indicates or reminds users that the special compartment has been allocated to hold the dental cleaning devices. Although placeholder indicators are useful, they are not necessary components of the invention. A person of ordinary skill in the art would also recognize that instead of the regular toothbrush, any other dental cleaning device (for example: an automated toothbrush, finger toothbrush, foldable toothbrush, one-time use toothbrush, dental floss, antiseptic/antibacterial mouthwash, cleaning bristles, dental cleaning twig, chewing stick, dental probiotic capsules, etc.) can also be placed in the exemplary food related accessory, i.e. a cutlery holder, without departing from the spirit and scope of the present invention.

Figure 32:
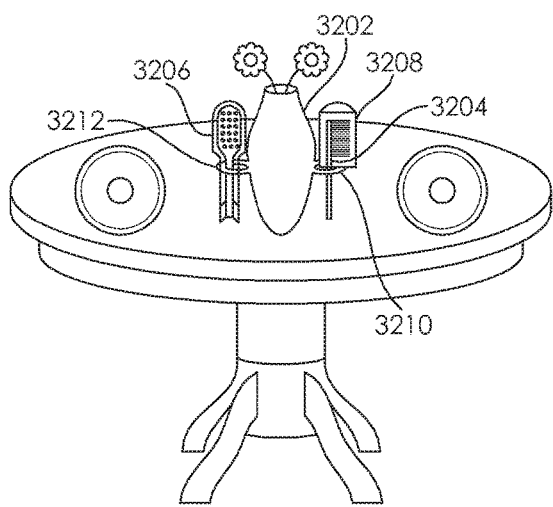
FIG. 32 illustrates exemplary multiple dental cleaning devices, a conventional toothbrush and a foldable toothbrush, hanging on an exemplary food related accessory, a dining table centerpiece, using the attachments. Note: Conventional toothbrush also has a cover for keeping bristles clean.

According to an embodiment of the present invention in FIG. 32, multiple dental cleaning devices in the form of a conventional toothbrush 3204 and a foldable toothbrush 3206 are shown hanging on an exemplary food related accessory, a dining table centerpiece 3202, using the attachments 3210, 3212. Such attachments 3210, 3212 illustrated in the figure include a round material with hole in the center, which can hold a dental cleaning device like a toothbrush, etc. and the attachments are affixed to the food related accessory, i.e. a dining table centerpiece, on one side. Such attachments can be made of any material and can have any shape as long as it can attach to or hold the dental cleaning device. The conventional toothbrush 3204 illustrated in the figure also has a cover 3308 for keeping bristles clean, however, the cover isn't necessary in all situations. Overall, this figure demonstrates how a user can attach a dental cleaning device to a food related accessory like a dining table centerpiece as long as that food related accessory is directly or indirectly involved with the food activities.

Figure 33:
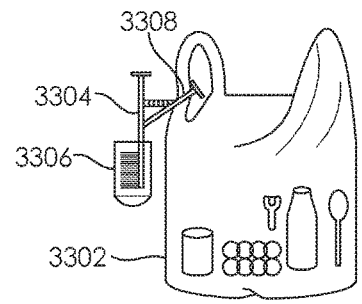
FIG. 33 illustrates an exemplary dental cleaning device, a conventional toothbrush with a cover for keeping bristles clean and a clip mechanism embedded at the bottom of the toothbrush handle that allows the toothbrush to be clipped to an exemplary bag (for example: a plastic bag) carrying either food, food container or food accessories.

According to an embodiment of the present invention in FIG. 33 an exemplary dental cleaning device in the form of a conventional toothbrush 3304 is shown with a cover 3306 for keeping bristles clean and a clip mechanism 3308 embedded at the bottom of the toothbrush handle that allows the toothbrush to be clipped to an exemplary bag i.e. a plastic bag 3302 carrying either food, food container or food accessories. The clip mechanism 3308 illustrated in the figure includes one of its arms as the base of the toothbrush itself, and the other arm of the clip is placed at an angle along with the spring in between the two arms, which allows the toothbrush to be clipped to any food accessory. The toothbrush with an embedded or attached clip can be clipped either outside or inside the food accessory, for example a bag. A person of ordinary skill in the art would recognize that rather than one arm of the clip being part of the toothbrush base itself, there can also be a stand-alone clip or another type of clip that can be affixed to the toothbrush. When the dental cleaning device with the embedded or attached clip is unclipped from the bag, it would also be possible to make the dental cleaning device stand straight using the clip as its base support. Clipping the dental cleaning device to the food accessories would make it easy for users to access the dental cleaning device. A person of ordinary skill in the art would recognize that other dental cleaning devices can have an embedded or attached clip (similar to the clip described above) and that would be within the spirit and scope of the present invention. A person of ordinary skill in the art would also recognize that a user would also be able to detach the clip attachment at any time from the dental cleaning device, and use the dental cleaning device on its own, without departing from the spirit and scope of the present invention.

Figure 34:
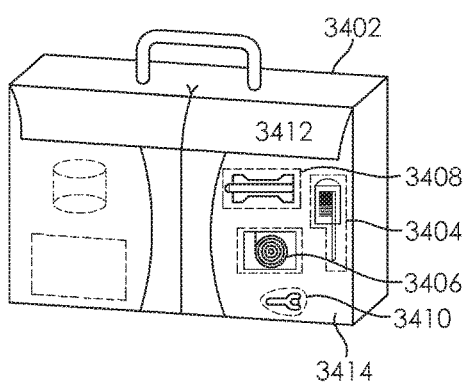
FIG. 34 illustrates exemplary dental cleaning devices, a conventional toothbrush with a cover for keeping bristles clean, a dental floss with a cover for keeping it clean, an antiseptic mouthwash and a Y shaped dental floss covered in plastic, inserted in the specially allocated dental cleaning device section in the front pouch of an exemplary bag carrying either food, food container or food accessories i.e. a laptop bag with food in its front pouch. In addition, the figure also illustrates an exemplary placeholder indicator on the laptop bag, indicating the dental cleaning device section where the dental cleaning devices can be kept.

According to an embodiment of the present invention in FIG. 34 exemplary dental cleaning devices in the form of a conventional toothbrush 3404 with a cover for keeping bristles clean, a dental floss 3406 with a cover for keeping it clean, an antiseptic mouthwash 3408 and a Y shaped dental floss 3410 covered in plastic are shown inserted in the specially allocated dental cleaning device section 3414 in the front pouch of an exemplary laptop bag. The dental cleaning device section 3414 allocated on the laptop bag can also include an exemplary placeholder indicator 3412 (for example: text referring to the dental cleaning device) on the laptop bag, indicating or reminding users that the special section has been allocated to hold the dental cleaning devices. Such exemplary placeholder indicators can also be in any other form of representation as long as they convey the intent of placing a dental cleaning device on the particular section of food accessory. Although placeholder indicators are useful, they are not necessary components of the invention.

Figure 35:
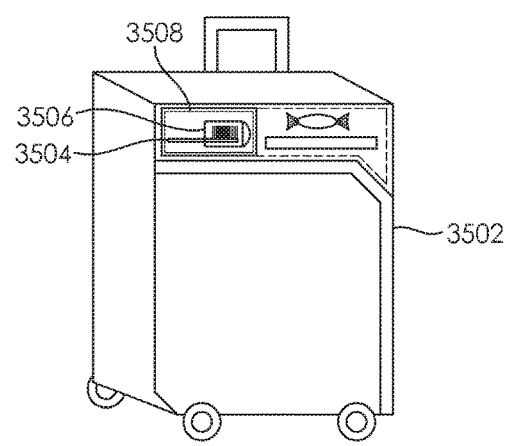
FIG. 35 illustrates an exemplary dental cleaning device, a conventional toothbrush with a cover for keeping bristles clean, inserted in a specially allocated dental cleaning device section of an exemplary bag carrying either food, food container or food accessories i.e. a hand luggage bag.

According to an embodiment of the present invention in FIG. 35, an exemplary dental cleaning device in the form of a conventional toothbrush 3504 is shown with a cover 3506 for keeping bristles clean, inserted in a specially allocated dental cleaning device section 3508 of an exemplary bag, i.e. a hand luggage bag 3502. The dental cleaning device section 3508 on the hand luggage bag can include an exemplary placeholder indicator (for example: an image of toothbrush, etc.), which would indicate or remind users that the dental cleaning devices can be kept in that section of the food accessory, and that would be within the spirit and scope of the present invention. The main intent of the indicators is to remind users that dental cleaning devices are important to maintain good oral health. Overall, this figure demonstrates how a user can insert dental cleaning devices in a bag.

Figure 36:
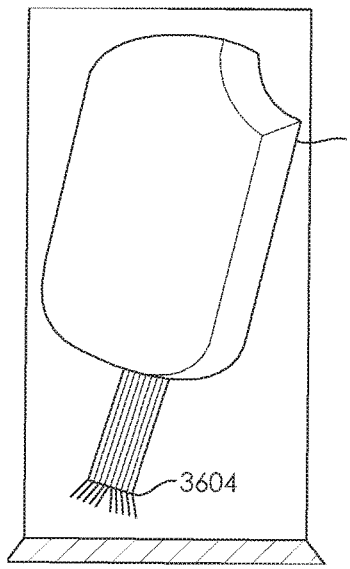
FIG. 36 illustrates an exemplary dental cleaning device, a cleaning stick, which is embedded in the center of an exemplary food product, an ice cream, instead of a regular wooden stick in the center.

According to an embodiment of the present invention in FIG. 36, an exemplary dental cleaning device in the form of a cleaning stick 3604 is shown, which is embedded in the center of an exemplary food product, an ice cream 3602. The cleaning stick 3604 can be used to clean teeth or gums after eating. A person of ordinary skill in the art would recognize that the cleaning stick 3604 can also be replaced with a toothbrush or another type of dental cleaning device without departing from the spirit and scope of the present invention. In such case, the bristles or the dental cleaning component of the dental cleaning device can also be completely embedded within the ice cream itself where the handle of the toothbrush also acts as the handle of the ice cream. Additionally, there can also be a cover/case on top of the toothbrush bristles in order to protect them, and then a user can take that cover/case off when they are done eating the ice cream and are ready to clean their teeth or gums. The entire cleaning stick or toothbrush can also be within a cover, and that cover can be embedded partially within an ice cream, and the rest of the cover can act as the handle for holding the ice cream. In this case, once the user is done eating the ice cream, they can take the dental cleaning device out of the cover and use it to clean their teeth or gums.

Figure 37:
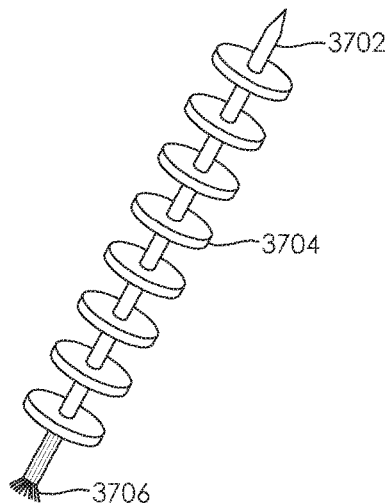
FIG. 37 illustrates an exemplary dental cleaning device, a cleaning stick, that's affixed (for example: glued) to the back of a kabab stick (skewers), which is further inserted in an exemplary food product, a kabab.

According to an embodiment of the present invention in FIG. 37, an exemplary dental cleaning device in the form of a cleaning stick 3706, that's affixed to the back of a kabab stick 3702, which is further inserted in an exemplary food product, a kabab 3704. In this case, once a user is done eating the kabab 3704, then they can use the cleaning stick 3706 to clean their teeth or gums.

Figure 38:
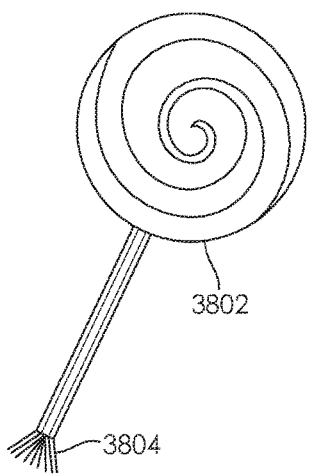
FIG. 38 illustrates an exemplary dental cleaning device, a cleaning twig, where a part of the cleaning stick is embedded on an exemplary food product, a lollipop chocolate, and the remaining part of the cleaning stick acts as a handle to hold the food product.

According to an embodiment of the present invention in FIG. 38, an exemplary dental cleaning device in the form of a cleaning stick 3804 is shown, where a part of the cleaning stick is embedded in an exemplary food product, a lollipop chocolate 3802, and the remaining part of the cleaning stick acts as a handle to hold the food product. In this case, once a user is done eating the lollipop chocolate 3802, they can use the cleaning stick 3804 to clean their teeth or gums.

Figure 39:
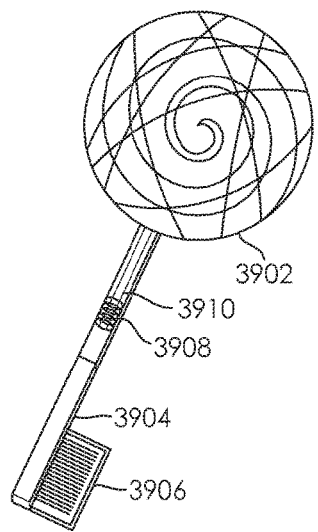
FIG. 39 illustrates an exemplary food product, such as a chocolate lollipop, and a dental cleaning device, a toothbrush, where the handle of that toothbrush is partly or fully enclosed in the hollow handle of an exemplary food product, such as a chocolate lollipop. It also shows the part of the toothbrush handle that is enclosed in the hollow handle of the lollipop is thinner in diameter such that it can fit within the hollow handle of the lollipop.

According to an embodiment of the present invention in FIG. 39, an exemplary dental cleaning device in the form of a conventional toothbrush is shown with a bristle cover 3906, where the handle of that toothbrush 3910 is partly or fully enclosed in the hollow handle 3908 of an exemplary food product, such as a lollipop chocolate 3902. In an embodiment where the toothbrush is partly enclosed in the hollow handle of the lollipop chocolate, the unenclosed portion of the toothbrush handle 3904 is visible outside the hollow handle of the lollipop chocolate. The toothbrush handle 3910 that is enclosed in the hollow handle 3908 of the lollipop chocolate 3902 will be thinner in diameter such that the toothbrush handle can fit within the hollow handle 3908 of the lollipop chocolate 3902.

Figure 41:
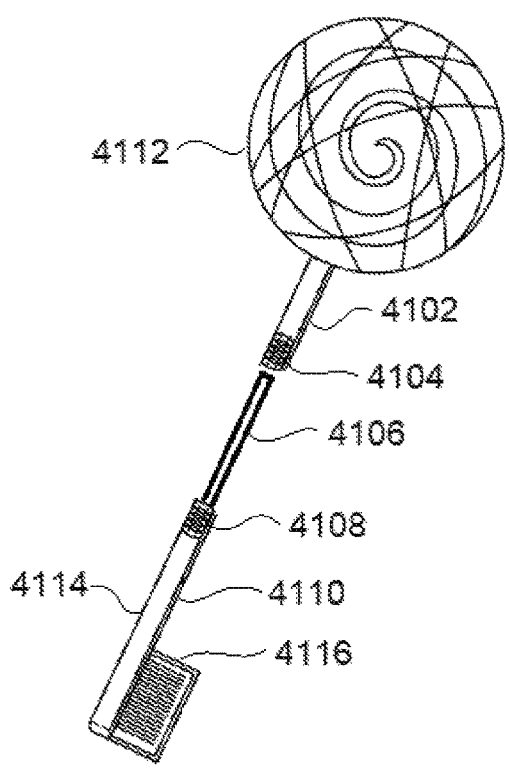
FIG. 41 illustrates a perspective view of a lollipop toothbrush apparatus according to an embodiment of the present invention.

According to an embodiment of the present invention as shown in FIG. 41, the end of the hollow handle 4102 of the lollipop chocolate 4112 has a threaded internal surface 4104 configured to receive at least part of the toothbrush handle 4110 which has complementary threading 4108. The toothbrush handle 4110 can thus be rotatably inserted or screwed into the hollow handle 4102 of the exemplary lollipop chocolate. When the toothbrush handle and the hollow handle of the lollipop are screwed together the unenclosed portion of the toothbrush handle 4110 and the hollow handle 4102 of the lollipop may form one continuous handle.

One or ordinary skill in the art would recognize that the visible part of the toothbrush handle 4110 and the hollow handle 4102 of the lollipop chocolate can be screwed or unscrewed from each other by twisting the toothbrush handle clockwise and counterclockwise respectively. When the visible part of toothbrush handle 4110 is rotated clockwise, it will screw the toothbrush handle 4110 to the hollow handle 4102 of the lollipop chocolate. When the visible part of toothbrush handle 4110 is rotated counter-clockwise, it will unscrew the toothbrush handle 4110 from the hollow handle 4102 of the lollipop chocolate.

At any time, a user can unscrew the toothbrush from the lollipop chocolate exposing more of the toothbrush handle 4106 for the user to grasp. For example, after a user has consumed the lollipop 4112, the user can unscrew the toothbrush from the hollow handle 4102 of the lollipop, which might be sticky due to eating of the lollipop. As the toothbrush is unscrewed, the toothbrush handle 4106 extends out of the lollipop handle 4102 giving the user a longer toothbrush handle to grasp. With this invention, once a user is done eating the lollipop, they can use the enclosed toothbrush to clean their teeth or gums.

The conventional toothbrush 4114 illustrated in FIG. 41 also has a cover 4116 for keeping bristles clean and protected from germs.

One or ordinary skill in the art would recognize that the toothbrush handle can also be completely enclosed inside the hollow handle of the lollipop chocolate. In this embodiment, the entire toothbrush handle would be invisible to the users until the toothbrush is unscrewed from the hollow handle of the lollipop chocolate.

Figure 42:
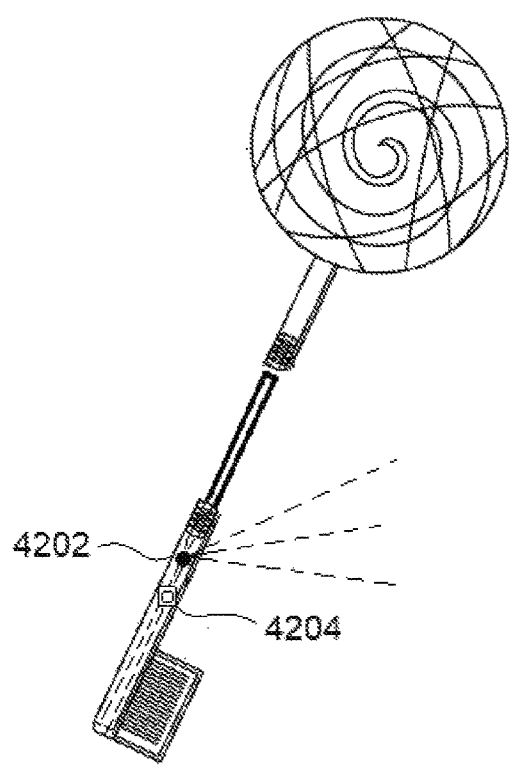
FIG. 42 illustrates a perspective view of a lollipop toothbrush according to another embodiment of the present invention.

According to an embodiment of the present invention as shown in FIG. 41 and FIG. 42, toothbrush handle will be made of transparent material and will include a built-in light 4202. According to this embodiment, the light 4202 inside the toothbrush handle automatically turns on when the toothbrush handle 4110 is unscrewed from the hollow handle 4102 of the lollipop. The current needed for such light 4202 to turn on would come from the batteries placed within the toothbrush handle assembly. Also, there will be a switch in the toothbrush handle assembly, which would block the current to flow to the light bulb when the toothbrush handle is screwed to the hollow handle of the lollipop. On the other hand, when the when the toothbrush handle is unscrewed from the hollow handle of the lollipop, then the switch in the toothbrush handle assembly would close the circuit and would allow the current to flow to the light bulb to turn it on.

The light inside the toothbrush handle can be programmed to automatically turn off the light after a predetermined time (for example: 2 minutes). It is to be understood that the emitting light can be of any color, and the light color can also be programmed to change after a certain duration. It is also to be clearly understood that instead of one bulb there can also be multiple bulbs as well as each light color can have its own bulb.

For example, when the toothbrush handle is unscrewed from the hollow handle of the lollipop chocolate, the light emitted is initially green for 1 minute, then changes to yellow for the next minute, and then changes to red for the next minute, and then turns off. Duration of 1 minute mentioned above is just exemplary and can be set to any duration.

As shown in FIG. 41 and FIG. 42, there may also be a button 4204 on the toothbrush handle to activate and deactivate the light 4202. For example, when the button 4204 is pressed light 4202 is emitted from the toothbrush handle 4110, and when the button 4204 is pressed again light 4202 ceases to be emitted from the toothbrush handle. In situation where the button 4204 is pressed to turn on light 4202 in toothbrush handle, it can still be programmed to automatically stop the light after a certain duration of time (for example: 2 minutes). Also, it can also be programmed to change the light color after predetermined time interval.

Similar to turning on of the light in the toothbrush handle, similar methodology can also be used to play music when the toothbrush handle is unscrewed from the hollow handle of the lollipop using speakers in the toothbrush handle and that would also be considered within the spirit and scope of the present invention.

Figure 43:
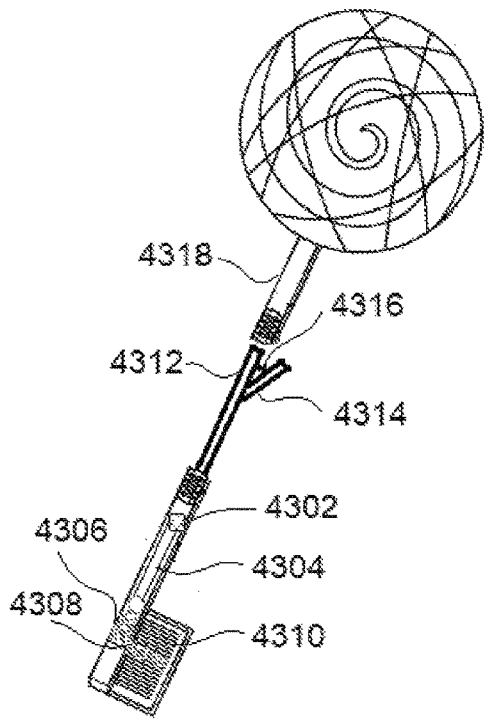
FIG. 43 illustrates a perspective view of a lollipop toothbrush according to another embodiment of the present invention.

According to an embodiment of the present invention as shown in FIG. 43, the toothbrush bristles 4310 will be covered with dry toothpaste or mouth freshener (for example: menthol, powdered fennel seeds, etc.). The toothpaste or mouth freshener will undergo a liquid drying process so that they can stick to the toothbrush bristles. In order to cover the bristles with dry mouth freshener, the mouth freshener would be first crushed to create a powder form and then it would be mixed with water to create a liquid form, and thereafter, the liquid mouth freshener would be poured on the toothbrush bristles 4310 and allowed to dry or will be dried using dryers, which would result in the mouth freshener to temporarily stick to the toothbrush bristles. Other products besides water can also be used along with the powdered toothpaste or mouth freshener to help them temporarily stick to the toothbrush bristles. Also, the toothpaste used above can be either non-edible or edible.

According to an embodiment of the present invention, there will be a hinged lever 4302 at the top of the toothbrush handle which would be attached to a rod 4304 inside the toothbrush handle. The rod may include a plunger for pushing toothpaste through the toothbrush handle towards the bristles. In other words, there will be toothpaste 4306 filled inside the handle of the toothbrush in the section right below the toothbrush bristles 4310 and when the lever 4302 is pushed forward, the rod 4304 and plunger attached to the lever would push the toothpaste 4306 out of the hole(s) 4308 in the toothbrush handle and onto the toothbrush bristles 4310.

According to an embodiment of the present invention as shown in FIG. 43, the portion of the toothbrush handle 4312 enclosed in the hollow handle 4318 of the lollipop chocolate can also have a compressed clip mechanism at its bottom, which would expand when the enclosed toothbrush handle 4312 is removed from the hollow handle 4318 of the lollipop chocolate. The clip mechanism will include the base of the toothbrush handle 4312 itself as one of its arms, and a second arm 4314 along with a spring 4316 in between the two arms. When the part of the toothbrush handle 4312 that's enclosed in the hollow handle 4318 of the lollipop chocolate is pulled out of the hollow handle 4318 of the lollipop chocolate, the second arm 4314 of the clip mechanism at the bottom of the toothbrush handle would open up since the compressed spring 4316 would get room to expand. The clip mechanism available at the bottom of the toothbrush handle 4312 will then allow the toothbrush to be clipped to any other objects once the handle of the toothbrush has been unscrewed from the hollow handle of the lollipop chocolate.

A person of ordinary skill in the art would recognize that rather than one arm of the clip mechanism being the toothbrush handle itself, there can also be a stand-alone clip or another type of clip that can be affixed to the toothbrush. Using the clips, it would also be possible to make the toothbrush stand straight using the clip as its base support. A person of ordinary skill in the art would also recognize that a user would also be able to detach the clip mechanism at any time from the toothbrush without departing from the spirit and scope of the present invention.

According to an embodiment of the present invention, the portion of the toothbrush handle enclosed in the hollow handle of the lollipop chocolate can also have a cap or cover at its end. The enclosed toothbrush handle may also be hollow and capable of storing fluid. A user would be able to open the cover or cap of the toothbrush handle mentioned above and use the fluid in the toothbrush handle to rinse their mouth after brushing their teeth.

According to an embodiment of the present invention, the portion of the toothbrush handle enclosed in the hollow handle of the lollipop chocolate can have multiple folds, which will be connected with a hinge in between the different folds of the handle. The folded portion of the toothbrush handle may be partially or fully enclosed in the hollow handle of the lollipop chocolate. A user will be able to unscrew the toothbrush handle from the hollow handle of the lollipop, and then unfold the toothbrush handle, or in other words, straighten the toothbrush handle at the hinge points, so the handle become long to be able to hold easily.

Figure 40:
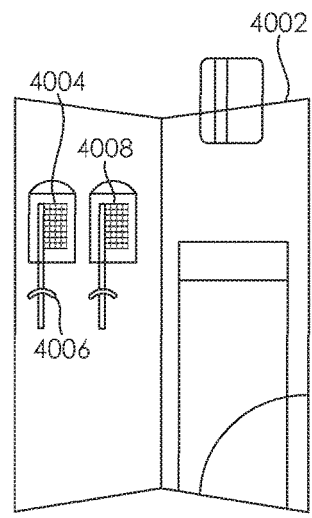
FIG. 40 illustrates exemplary dental cleaning devices, i.e. multiple toothbrushes along with bristle covers, where each toothbrush is inserted using individual attachments on an exemplary food related accessory, a restaurant bill/check holder. In addition, the figure also illustrates that an exemplary dental cleaning device, i.e. a toothbrush, can also include mouth freshener covered bristles.

According to an embodiment of the present invention in FIG. 40, exemplary dental cleaning devices in the form of multiple toothbrushes 4004 with bristle covers are shown, where each toothbrush is inserted using individual attachments 4006 in an exemplary food related accessory, a restaurant bill/check holder 4002. The restaurant bill/check holder is usually presented to the patrons after the food is consumed, and can have several small attachments 4006 affixed to it such that they can hold multiple dental cleaning devices 4004. The attachments 4006 can be made of any material and can have any shape as long as they can attach to or hold the dental cleaning devices. Users would be able to take the dental cleaning devices out of the bill/check holder attachments and use them to clean their teeth or gums. A person of ordinary skill in the art would recognize that the attachments 4006 illustrated inside the bill/check holder can also be outside the bill/check holders without departing from the spirit and scope of the present invention.

Additionally, as shown in FIG. 40, the toothbrush/toothbrushes 4004 can include bristles that are covered with dry mouth freshener 4008 (for example: menthol, powdered fennel seeds, etc.

Overall, note that any of these embodiments shown in this invention are just exemplary of the broader invention, however, they do illustrate that any dental cleaning device can be easily held on the food accessories, providing a visual reminder to the users to frequently clean their teeth or gums and also making the dental cleaning devices within easy access of the users. This easy access of dental cleaning devices can indirectly enable the users to frequently clean their teeth or gums, and therefore, avoid a lot of dental problems and their associated expenses.

Additionally, A person of ordinary skill in the art would recognize that there are many different types of dental cleaning devices, food utensils, food containers, food accessories, bags used for carrying foods or food containers or food accessories, and the food products themselves, etc. Therefore, rather than limiting the invention to just the embodiments shown in this document, it is to be clearly understood that all other dental cleaning devices, food utensils, food containers, food accessories, bags used for carrying foods or food containers or food accessories, food products themselves, etc. would also be within the spirit and scope of the present invention.

In addition, A person of ordinary skill in the art would recognize that any of the illustrated figures of this invention can also have substitute components, combinations and/or features as long as the intent of holding a dental cleaning device on the food accessory is maintained.

Insubstantial changes from the claimed subject matter as viewed by a person with ordinary skill in the art, now known or later devised, are expressly contemplated as being equivalently within the scope. Therefore, obvious substitutions now or later known to one with ordinary skill in the art are defined to be within the scope and spirit of the invention.

What is claimed is:

1. A lollipop toothbrush apparatus:
   an edible lollipop head;
   a hollow handle extending from the lollipop head, said handle having an internal threaded wall configured to receive a complementary threaded member;
   a toothbrush comprising a handle and a brush head, the toothbrush handle comprising:
      a lower segment dimensioned to snugly fit inside the hollow handle of the lollipop head, and
      an upper segment comprising:
         a threaded portion which rotatably engages with the internal threads of the hollow handle, and
         a non-threaded portion having the same longitudinal cross-sectional area as the hollow handle, wherein said threaded portion is configured to be rotatably inserted into the hollow handle of the lollipop,
   wherein the threaded portion of the upper segment is configured to screw into the hollow handle until the non-threaded portion is reached, at which point the hollow handle of the lollipop and the upper segment of the toothbrush handle form a combined continuous handle for the lollipop.

2. The lollipop toothbrush apparatus of claim 1, wherein the brush head and the lollipop head are at opposite ends when the toothbrush is inserted into the hollow handle.

3. The lollipop toothbrush apparatus of claim 2, wherein the toothbrush handle further comprises an integrated light.

4. The lollipop toothbrush apparatus of claim 3, wherein the toothbrush handle further comprises a button for turning the light on and off.

5. The lollipop toothbrush apparatus of claim 4, wherein said light is programmed to change colors at the end of a predetermined time interval.

6. The lollipop toothbrush apparatus of claim 1, wherein the toothbrush handle further comprises a spring-loaded clip that gets compressed when the toothbrush handle is inserted into the hollow handle of the lollipop.

7. The lollipop toothbrush apparatus of claim 1, wherein said toothbrush is at least partly hollow and configured to house toothpaste.

8. The lollipop toothbrush of claim 7, wherein the brush head includes bristles and a base with one or more openings proximate the bristles.

9. The lollipop toothbrush of claim 8, wherein a lever is attached to the toothbrush which is connected to a plunger inside the toothbrush handle, wherein said lever is configured to move the plunger through the hollow section of the toothbrush and push the toothpaste through the one or more openings in the base of the brush head.

* * * * *